(12) United States Patent
Zehnder et al.

(10) Patent No.: US 9,289,325 B2
(45) Date of Patent: Mar. 22, 2016

(54) EXTRAOCULAR EPIRETINAL IMPLANT

(75) Inventors: Thomas Zehnder, Bäch (CH);
Hans-Jurgen Tiedtke, Bonn (DE)

(73) Assignee: PIXIUM VISION SA, Paris (FR)

( * ) Notice: Subject to any disclaimer, the term of this patent is extended or adjusted under 35 U.S.C. 154(b) by 1075 days.

(21) Appl. No.: 11/988,634

(22) PCT Filed: Jun. 2, 2006

(86) PCT No.: PCT/EP2006/005273
§ 371 (c)(1),
(2), (4) Date: Jun. 23, 2009

(87) PCT Pub. No.: WO2007/006376
PCT Pub. Date: Jan. 18, 2007

(65) Prior Publication Data
US 2011/0152969 A1      Jun. 23, 2011

(30) Foreign Application Priority Data

Jul. 14, 2005   (DE) .......................... 10 2005 032 989

(51) Int. Cl.
*A61N 1/36* (2006.01)
*A61F 9/08* (2006.01)
(Continued)

(52) U.S. Cl.
CPC . *A61F 9/08* (2013.01); *A61N 1/025* (2013.01); *A61N 1/0543* (2013.01); *A61N 1/36046* (2013.01); *A61N 1/37229* (2013.01); *A61N 1/3787* (2013.01)

(58) Field of Classification Search
CPC ..... A61N 1/36046; A61N 1/0543; A61F 9/08
USPC .............................. 607/53, 54, 141; 623/6.63
See application file for complete search history.

(56) References Cited

U.S. PATENT DOCUMENTS 5,935,155 A    8/1999   Humayun et al.
6,298,270 B1   10/2001  Nisch et al.
(Continued)

FOREIGN PATENT DOCUMENTS

CA      2407360     11/2001
CA      2538157     3/2005
(Continued)

OTHER PUBLICATIONS

International Search Report for International Application No. PCT/EP2006/005273, date of mailing Feb. 7, 2007; 3 pages.

*Primary Examiner* — Tammie K Heller
(74) *Attorney, Agent, or Firm* — Workman Nydegger

(57) ABSTRACT

A visual prosthesis in the form of a retinal implant, which is distinguished by the least possible space requirement inside the eye, is achieved by a visual prosthesis having an intraocular implant and an extraocular implant, which supplies the intraocular implant with energy and controls it. Virtually all the electronic components, which do not necessarily need to be accommodated with the intraocular implant inside the eye, can be arranged outside the eyeball, for example on the sclera. In this way, the space requirement of the stimulation system inside the eye is reduced and the operative intervention for implanting the stimulation system inside the eye is kept as small as possible. A bidirectional inductive interface between an extracorporeal part of the visual prosthesis and an intracorporeal part, including the intraocular and extraocular implants, via which a current supply and bidirectional data transmission can be carried out is provided.

69 Claims, 6 Drawing Sheets

(51) Int. Cl.
  *A61N 1/02* (2006.01)
  *A61N 1/05* (2006.01)
  *A61N 1/372* (2006.01)
  *A61N 1/378* (2006.01)

(56) References Cited

U.S. PATENT DOCUMENTS

| | | | |
|---|---|---|---|
| 6,458,157 B1 | 10/2002 | Suaning | |
| 7,027,773 B1* | 4/2006 | McMillin | 455/41.2 |
| 7,248,928 B2 | 7/2007 | Yagi | |
| 2002/0091421 A1 | 7/2002 | Greenberg et al. | |
| 2002/0169486 A1* | 11/2002 | Chow et al. | 607/54 |
| 2003/0093132 A1* | 5/2003 | Eckmiller | 607/54 |
| 2003/0124445 A1* | 7/2003 | Sugimura et al. | 430/56 |
| 2003/0158588 A1 | 8/2003 | Rizzo et al. | |
| 2003/0181957 A1* | 9/2003 | Greenberg et al. | 607/54 |
| 2004/0106965 A1* | 6/2004 | Chow | 607/54 |
| 2004/0127957 A1* | 7/2004 | Fujikado et al. | 607/54 |
| 2005/0004626 A1 | 1/2005 | Terasawa et al. | |
| 2005/0283208 A1* | 12/2005 | Von Arx et al. | 607/60 |

FOREIGN PATENT DOCUMENTS

| | | |
|---|---|---|
| CA | 2611851 | 2/2011 |
| DE | 19705988 | 4/1998 |
| DE | 10296600 | 4/2004 |
| DE | 10315397 | 10/2004 |
| EP | 1 386 636 A2 | 2/2004 |
| JP | 11-0506662 | 6/1999 |
| JP | 2002505910 | 2/2002 |
| JP | 2002539859 | 11/2002 |
| JP | 2003-531697 | 10/2003 |
| JP | 2004057628 | 2/2004 |
| JP | 2004521673 | 7/2004 |
| WO | WO 96/39221 A1 | 12/1996 |
| WO | WO 98/17343 | 4/1998 |
| WO | WO 99/45870 | 9/1999 |
| WO | WO 00/56393 | 9/2000 |
| WO | WO 02/40095 A1 | 5/2002 |
| WO | WO 02/080828 | 10/2002 |
| WO | WO 03/039661 A1 | 5/2003 |
| WO | WO 03/061537 A1 | 7/2003 |

* cited by examiner

EXTRAOCULAR EPIRETINAL IMPLANT

CROSS REFERENCE TO RELATED APPLICATIONS

This application is the U.S. national stage application of PCT/EP2006/005273, Published as WO 2007/006376, filed Jun. 2, 2006, which claims priority to German patent Application Number 10 2005 032 989.6, filed Jul. 14, 2005, herein incorporated by reference in its entirety.

BACKGROUND OF THE INVENTION

The present invention relates to a device for implantation in a human eye, having an electrode array or a microcontact structure for contacting nerve tissue in the visual system of the human eye. The present invention relates in particular to a visual prosthesis having a device for generating stimulation impulses, which are used to stimulate living tissue or nerves.

One frequent cause of the partial or full loss of eyesight is destruction of the photoreceptor layer in the retina of the human eye, after which incident photons are not converted into a corresponding stimulation of the ganglion cells. The ganglion cells are only partly affected by this pathology, so that an external stimulation of the ganglion cells still existing in the retina can generate a visual perception. On the basis of this, developments which involve the implantation of a microcontact structure for contacting intact ganglion cells have been carried out for some time.

Devices have already been developed in the form of implants for the retina of the human eye, which are intended for the treatment of patients who have partially or fully lost their eyesight owing to defects in the retina. A microelectronic device is in this case implanted in the region of the retina with a multiplicity of photosensitive pixel elements, via which an image projected onto the retina through the still intact lens of the eye is captured. In other visual prostheses, the image capturing is carried out using an external camera, in particular a video camera. The image captured by the pixel elements or the camera is converted into electrical signals and delivered via stimulation electrodes by means of electrical stimulation impulses to the ganglion cells of the retina or to the optic nerve, so as to restore or improve the eyesight of the blind or partially blind patient.

For epiretinal transmission of the stimulation impulses to the cells of the retina or to the cells of the optic nerves, microcontact structures are used which essentially consist of a support material that carries electrically conductive contact elements designed in the form of pins or needles on one side, which protrude from the plane of the support sheet and are distributed uniformly with a constant area density over the surface of the implant. The known visual prostheses, however, have the disadvantage that they entail a large space requirement. Owing to the particular sensitivity of the human eye and the extremely limited space inside the eye, it is in principle desirable to accommodate stimulation systems or the implants of the visual prostheses in as small a space as possible.

Another problem with known visual prostheses consists in supplying energy to the implants and their microcontact structure, or the surface of the electrodes. According to the present state of knowledge, an average power of about 40 mW is necessary for the energy supply of a retinal implant. Such a energy supply cannot be provided over a prolonged period of time by means of an implanted battery, since this would entail too great a space requirement.

Active retinal implants therefore require a energy supply unit which is independent of the system for generating the visual impression, lies outside the eye and operates without a wire connection to the retinal implant. DE 19705988 C2 discloses a subretinal implant, the implant being provided with a photovoltaic layer which is effective for light outside the visible spectrum. The energy supply is in this case carried out using infrared light. The retinal implant is provided with a surface tightly attached to the retina, the surface being provided with electrodes for stimulating cells of the retina. The current supply of the components of the implants inside the eye using infrared light may, however, entail the risk of thermal damage to the eye due to local heating inside the eye.

BRIEF SUMMARY OF EMBODIMENTS OF THE INVENTION

It is therefore an object of the present invention to provide a visual prosthesis in the form of a retinal implant, which is distinguished by the least possible space requirement inside the eye. It is another object of the present invention to provide an implant system whose current supply impedes the eye's freedom of movement in the eye socket as little as possible.

The present invention achieves the aforementioned object by a visual prosthesis with a stimulation system for implantation in a human eye, having an electrode array for contacting and stimulating living tissue or nerves in the visual system of the eye, which generates stimulation impulses by means of an electrical circuit, the stimulation system comprising at least one intraocular implant and at least one extraocular implant, which supplies the intraocular implant with energy.

The present invention provides a neurostimulation device for the stimulation of still existing ganglion nerve cells, which can improve eyesight if there is degenerate retinal damage but there are still intact optic nerves. By separating the implant into an epiretinal part and an extraocular part, a multiplicity of the necessary components and the greatest volume of the implant can be located in the outer, extraocular part of the implant. With the aid of the implant according to the invention, potential damage to the retina or other sensitive structures of the eye when arranging the stimulation system can be minimised.

The visual prosthesis according to the invention therefore offers the advantage that virtually all the electronic components, which do not necessarily need to be accommodated with the intraocular implant inside the eye, can be arranged outside the eyeball, for example on the so-called sclera. In this way, the space requirement of the stimulation system inside the eye is reduced and the operative intervention for implanting the stimulation system inside the eye can be kept as small as possible. Another advantage of the visual prosthesis according to the invention is that the current supply of the intraocular implant can be carried out via the extraocular implant, without impeding the eye's freedom of movement in the eye socket. The visual prosthesis according to the invention furthermore allows substantially non-injurious maintenance or replacement of the stimulation system, for example when the extraocular implant is intended to be replaced by a more modern version.

The extraocular part of the implant is arranged on the sclera at the outer periphery of the eye, so that the movement of the eyeball is compromised as little as possible. It is particularly advantageous, if the extraocular part of the implant is placed in the adipose tissue surrounding the eye between two muscles, which are used for moving the eye. The extraocular implant may be sutured externally onto the sclera of the eye.

In this way, unimpeded and painless movement of the eye inside the eye socket is possible.

The individual implant parts inside and outside the eye may preferably be coupled to one another via a wire connection (with or without a plug connector). When the implant according to the invention is in the implanted state, this wire connection is preferably fed through the eye in the region of the pars plana, in the vicinity of the iris where no retina is present. The transfer both of the energy, i.e. the current supply, and the image data between the extraocular implant outside the eye and the further electronics may be carried out wirelessly by inductive means. The wireless transmission of energy and image data from the electronics remote from the eye to the implant avoids cable movements and concomitant impediments or damage.

The other electronics of the visual prosthesis, which are required for processing and preparing the image data captured by an external camera, may be arranged remotely from the eye outside the body. The electronic components may for example be accommodated in a so-called pocket computer, which may be carried in a separate pocket on the body. The electronic components are particularly advantageously accommodated in a spectacle frame, which also contains the camera that captures the image data.

Since the electronic components, which are required for image-processing the signals delivered by the video camera, are located outside the body, their maintenance or replacement by a more modern version of the electronic interface is straightforward. The components of the electronic interface may be adapted individually to the respective electronic stimulation level of the implant system. In this way, it is possible to ensure a minimal level of electrical charge for all the electrodes in the electrode array, so that the tissue or nerve cells stimulated by the electrical stimulation impulses are stressed as little as possible. It is thus possible to avoid damage on the retina of the eye in the vicinity of the electrodes due to an elevated charge level, as well as painful sensations for the patient.

In principle, image acquisition in the stimulation system according to the invention is carried out by an external camera, the image signals of which are delivered after electronic preprocessing via the extraocular implant and the epiretinal implant to the retina of the eye. The epiretinal implant comprises an integrated electrode array which stimulates the ganglion cells or the cells of the retina by electrical signals in a position-resolved way according to the received image data, and thereby forwards the image captured by the external camera to the nerves of the visual system. A particular advantage of the active epiretinal implant is that it can be adapted to various conditions in respect of the ambient luminance.

The intraocular implant comprises an electrode array having a number of stimulation electrodes, which are preferably arranged close together in a matrix. The electrode array comprises a microcontact structure with a number of contact sites, via which the stimulation electrodes are in contact with the retinal cells or ganglion cells and stimulate the contacted retinal cells or ganglion cells by means of stimulation impulses. The outer region of the microcontact structure for epiretinal contacting of the ganglion cells is adapted to the outer contour of the foveal region of the retina, and may have a spherical shape. The microcontact structure, or the electrode array, of the epiretinal implant is in this case preferably arranged in the region of the macula of the eye. The macula is the place inside the eye, or on the retina, which receives the greatest amount of light; it is therefore often referred also referred to as the "place of sharpest vision".

The extraocular implant is equipped with an electrical control unit, which is preferably designed as a digital control unit with analogue auxiliary functions and generates stimulation impulses with the aid of the image data captured by an external camera. To this end, the electrical control unit comprises at least one current or voltage source and at least one impulse generator that generates electrical stimulation impulses, which are amplified by the current/voltage source to form stimulation impulses or stimulation currents and are forwarded to the stimulation electrodes in the electrode array in the intraocular implant. The electrical control unit may also be equipped with electronic storage means, in which the calculated duration and intensity of the stimulation impulses to be generated are stored and can be called in response to a particular instruction. Expediently, the electronic components of the electrical control unit are accommodated at least partially in an integrated circuit by being photolithographically microstructured, and preferably on a chip in the extraocular implant. The extraocular implant has at least one counter-electrode, which serves as a return current path for the stimulation electrodes.

The electrical control unit has a contact pad for each stimulation electrode, i.e. a connection surface via which a stimulation electrode can respectively be contacted by a separate wire connection. The wire connection is designed as a flexible implant and is fed between the extraocular implant and the intraocular implant into the interior of the eye, preferably in the region of the pars plana where no retina is present so as to avoid compromising the retina.

Feeding the wire connection between the epiretinal implant and the extraocular implant through the sclera of the eye in the region of the pars plana represents an intervention with the least outlay and the least possible damage to the eye. The danger of complications and the infection risk during the operation are therefore also reduced. If the flexible implant of the wire connection is fastened together with the inner and outer parts of the implant on the eye, these execute the same movements as the eye so that the eye's freedom of movement is not compromised either by the wire connection or by the inner and outer parts of the implant.

The wire connection for coupling the extraocular implant to the intraocular implant comprises at least one line for transmitting the operating current and at least one signal line for transmitting image data and/or electrical stimulation impulses from the digital control unit to the intraocular implant. According to a preferred embodiment of the present invention, besides the electrical lines for transmitting the operating current, the wire connection also comprises at least as many lines for transmitting electrical stimulation impulses as there are stimulation electrodes provided in the intraocular implant. The wire connection may furthermore comprise one or more optical fibers for unidirectional or bidirectional data transmission by means of light signals between the extraocular part and the intraocular part of the implant.

In order to ensure reliable fixing of the flexible implant with the electrode array or the microcontact structure and the wire connection between the microcontact structure and the extraocular implant, the intraocular implant and/or the flexible implant of the wire connection may be fixed inside the eye with the aid of a nail, a so-called tack. To this end, the tack is operatively fitted from inside the eye and extends through the flexible implant and the retina into the choroid or the sclera of the eye, where it is anchored by its retaining hooks.

The intraocular implant comprises a number of photosensitive elements, which drive the contact sites of the electrode array via the electrical circuit as a function of light incident on the intraocular implant. At least one light receiver of the intraocular implant is in this case capable of receiving light signals of a light transmitter from outside the eye. According to a preferred embodiment, the light receiver of the intraocular implant is designed as an infrared receiver which receives infrared signals of an infrared transmitter from outside the eye, preferably via the natural light path of the eye.

In this way, the interface between the light transmitter outside the eye and the photosensitive elements, or the light receiver, of the intraocular implant can transfer image data captured by an external camera via light signals from the light transmitter outside the eye to the photosensitive elements or the light receiver of the intraocular implant. Infrared light is preferably used for transmitting the image data, since it lies outside the visible light spectrum and therefore does not irritate any remaining eyesight of the patient and the transmission of the image data.

Signal processing of the received image data takes place in the extraocular implant, including signal amplification, for which reason external energy input is necessary. This energy input is carried out wirelessly in the visual prosthesis according to the invention through the inductive interface between an external radiofrequency transmitter coil and the radiofrequency receiver coil of the extraocular implant. To this end, according to another preferred embodiment of the visual prosthesis according to the invention, an antenna remote from the stimulation system is provided for an inductive interface, which can transmit electromagnetic signals preferably in the radiofrequency range. The extraocular implant is furthermore equipped with an antenna, which can receive electromagnetic signals preferably in the radiofrequency range.

The radiofrequency antenna of the extraocular implant receives the radiofrequency electromagnetic signals emitted by the transmitter antenna of the electronics outside the body. This creates an inductive current which supplies the implant on the eye with sufficient energy. The current resulting from the induction is transferred from the outer part of the implant via the wire line to the inner part of the implant, in order to supply the electrode array and the infrared receiver with current.

The inductive interface between the antenna outside the eye and the antenna of the extraocular implant may also be designed bidirectionally, in that the antenna remote from the stimulation system can receive electromagnetic signals preferably in the radiofrequency range and the antenna of the extraocular implant can transmit electromagnetic signals preferably in the radiofrequency range. In this preferred embodiment, the extraocular implant is designed so that it can transfer information, for example about operating parameters of the stimulation system, via the inductive interface. According to another particular embodiment of the invention, the data rate of the signals received by the antenna of the extraocular implant is different from the data rate of the signals transmitted by the antenna of the extraocular implant.

In the case of a bidirectional inductive interface, both the outer part of the implant on the eye and the electronics outside the body are therefore equipped with a transmission unit and a reception unit, which can respectively transmit and receive electrical signals preferably in the radiofrequency range. Signals generated by the epiretinal implant inside the eye can therefore also be transferred via the wire line to the outer part of the implant, and forwarded from there via the transmission unit in the form of radiofrequency signals to the electronics outside the body.

The electronics outside the body receive the radiofrequency signals from the transmitter of the extraocular implant via their receiver unit, and feed them to a central computation unit where the signals are evaluated. In this way, signals, which provide information for example about a sufficient current supply of the internal implant, the quality of the received image signals, the function of the stimulation electrodes in the electrode array, the efficiency of the inductive interface or the contact of the stimulation electrodes with the ganglion cells, can be transferred from the epiretinal implant inside the eye.

The intraocular implant may furthermore comprise at least one light-emitting element, which radiates light signals as a function of operating parameters of the stimulation system. To this end, the light signals emitted by the light-emitting element are encoded as a function of operating parameters of the intraocular implant, for example by modulating the duration and/or intensity of the light signals. The light signals emitted by the light-emitting element may for example contain information about the position of the intraocular implant, about the quality of the image data received by the intraocular implant, about the quality of the current supply of the intraocular implant and/or about the impedance or the electrical resistance of the stimulation electrodes. The light signals emitted by the light-emitting element may furthermore contain information about the function of the stimulation electrodes in the electrode array and about the contact of the stimulation electrodes with the ganglion cells.

This light-emitting element is preferably arranged inside the eye so that the light signals emitted by the light-emitting element can be detected by an observer via visual contact into the interior of the eye. The light-emitting element is preferably designed as a diode (status diode) that radiates light, in particular infrared light, which can be detected by a light receiver, in particular by an infrared light receiver outside the eye.

According to another aspect of the invention, the aforementioned objects are furthermore achieved by a method for operating the device according to the invention, comprising at least the following steps:

capturing an image using an external camera, generating position-resolved image data from the captured image, calculating diagnostic instructions, control instructions or stimulation instructions with a particular duration and intensity as a function of the image data, transferring the diagnostic instructions, control instructions or stimulation instructions to a stimulation system having an intraocular implant and an extraocular implant, calculating and generating electrical stimulation impulses or stimulation currents with a particular duration and intensity in the extraocular implant or carrying out diagnostic tasks according to the diagnostic instructions, control instructions or stimulation instructions, transferring the electrical stimulation impulses or stimulation currents to the intraocular implant, and applying the electrical stimulation impulses or stimulation currents to at least one stimulation electrode in the intraocular implant so that at least one retinal cell or ganglion cell, which is in contact with the relevant stimulation electrode, is stimulated.

In order to prepare the image data captured by the external camera for use in the stimulation system, before transfer to the stimulation system they are electrically evaluated or processed in the electrical control unit in order to generate corresponding electrical stimulation impulses or stimulation currents. In this case the components of the electrical control unit may on the one hand be part of the extraocular implant, or on the other hand accommodated in an external computation unit which the patient carries with them separately, or accommodated in spectacles on which the external camera and/or the light transmitter for the infrared interface is also arranged.

As described above, in the method for operating the device according to the invention, the current required for operation of the extraocular implant and the intraocular implant is transmitted wirelessly via an inductive interface between the radiofrequency transmitter antenna outside the eye and the radiofrequency receiver antenna of the extraocular implant, while the image data captured by the external camera are transmitted wirelessly via an infrared interface between the infrared transmitter outside the eye and the infrared receiver inside the eye. As an alternative, the image data captured by the external camera may likewise be transmitted wirelessly via the inductive interface between the radiofrequency transmitter antenna outside the eye and the radiofrequency receiver antenna of the extraocular implant.

The image data captured by the external camera or the diagnostic instructions, control instructions or stimulation instructions may be transmitted as a serial data stream from the infrared receiver inside the eye via the wire connection to the digital control unit in the extraocular implant. In this case, the serial data stream from the infrared receiver inside the eye via the wire connection to the digital control unit in the extraocular implant contains information about the electrode address, for example from 1 to 250, and about the amplitude associated with the electrode address, for example from 0 to 1000 .mu.A, of the stimulation impulses for the relevant stimulation electrode. With the aid of the information relating to the electrode address and the amplitude of the stimulation impulses, stimulation impulses with a particular duration and intensity are calculated and generated by the electrical control unit of the extraocular implant for each stimulation electrode. The shape or the profile of the electrical stimulation impulses is adapted to the ganglion cells to be stimulated. Using a multiplicity of current generators in the extraocular implant, electrical current with a particular intensity and duration is applied to the stimulation electrodes.

The stimulation impulses or stimulation currents are transferred as a parallel signal stream from the electrical control unit of the extraocular implant via parallel wire connections to the stimulation electrodes in the intraocular implant. To this end, the electrical control unit of the extraocular implant, or the retinal stimulator chip, has for example 250 connection pads to which wires for 250 stimulation electrodes in the electrode array of the intraocular implant can respectively be connected.

In a preferred embodiment of the method, it is also possible for the intraocular implant to transfer diagnostic data relating to operating parameters of the intraocular implant via the wire connection to the extraocular implant, for example as a serial data stream. The serial diagnostic data stream is subsequently forwarded inductively, for example using load modulation, from the extraocular inductive coil to external diagnostic means which are for example accommodated in the spectacles. As an alternative to the inductive feedback path described above, the status light-emitting diode in the intraocular part of the implant may also be used as an optical return channel with a digital reception unit and digital evaluation unit in the spectacles.

Other Preferred Embodiments of the Implant According to the Invention

As already described above, electronic components of the visual prosthesis according to the invention may in particular be accommodated in a module outside the body, preferably in spectacles which the patient may wear like a normal visual aid. The electronic components accommodated in a module outside the body will be referred to below as the extracorporeal part of the visual prosthesis according to the invention, while the components of the visual prosthesis according to the invention which are arranged inside the body, comprising the components implanted intraocularly in the eye and those implanted extraocularly in the eyeball, will be summarised as the intracorporeal part of the visual prosthesis according to the invention.

Between the extracorporeal part (for example in the spectacles) of the visual prosthesis and the intracorporeal part in or on the patient's eye, there is a wireless inductive interface via which both the energy is input and also data transmission is carried out. According to a preferred embodiment of the present invention which has already been described, this inductive interface between the extracorporeal part and the intracorporeal part is designed bidirectionally. To this end, both the extracorporeal part and the intracorporeal part are equipped with a transmitter coil which can transmit electrical signals preferably in the radiofrequency range, and with a receiver coil or an antenna which can transmit electrical signals preferably in the radiofrequency range. In this way, electrical signals can be transferred both from the extracorporeal part to the intracorporeal part and in the opposite direction, from the intracorporeal part to the extracorporeal part of the visual prosthesis according to the invention (bidirectionality). Both in the extracorporeal part and in the intracorporeal part, it is also possible to provide only a transmitter-receiver coil which respectively fulfils both functions of transmitting and receiving electrical signals.

In a refinement of this preferred embodiment of the present invention, the bidirectional data line between the extracorporeal part and the intracorporeal part of the visual prosthesis comprises at least two preferably wireless transmission channels. In this case, at least one wireless transmission channel extends from the extracorporeal part (for example in the spectacles) to the intracorporeal part of the visual prosthesis in the eye, also referred to below as the "forth transmission channel" (up-link), and at least one wireless transmission channel extends from the intracorporeal part of the visual prosthesis in the eye to the extracorporeal part in the spectacles, also referred to below as the "back transmission channel" (down-link).

The data transmission between the extracorporeal part and the intracorporeal part of the visual prosthesis is preferably carried out simultaneously, i.e. data are transmitted at the same time both on the forth transmission channel (up-link) and on the back transmission channel (down-link). The back transmission channel (down-link) may be used in particular to transfer data about the status of the intracorporeal part of the visual prosthesis. This provides an additional safety factor, in that the status and the functionality of the intracorporeal part of the visual prosthesis can be constantly monitored and a corresponding malfunction can be signalled in the event of failure of the visual prosthesis or the back transmission channel (down-link).

In another preferred embodiment of the present invention, the data transmission between the extracorporeal part and the intracorporeal part of the visual prosthesis may take place alternately. For example, the forth transmission channel (up-link) from the extracorporeal part to the intracorporeal part may be active during particular time periods, and the back transmission channel (down-link) from the intracorporeal part to the extracorporeal part of the visual prosthesis may be active during other particular time periods. With this alternating data transmission, it is also possible to provide only one transmission channel since this can then be used alternately either as an forth transmission channel (up-link) or as a back transmission channel (down-link).

During normal operation, the data transmission between the extracorporeal part and the intracorporeal part of the visual prosthesis predominantly takes place by means of the forth transmission channel (up-link), i.e. the image data captured and processed by the extracorporeal part of the visual prosthesis (for example in the spectacles) are transferred or transmitted via the forth transmission channel (up-link) to the intracorporeal part of the visual prosthesis (in the eye). On the back transmission channel (down-link), conversely, transmission is carried out only in the event of a feedback from the intracorporeal part to the extracorporeal part of the visual prosthesis, for example when the intention is to transfer data about the status of the intracorporeal part of the visual prosthesis or an error message.

Various types of data may be transmitted on the forth transmission channel (up-link) from the spectacles to the implant in the eye. For example, stimulation instructions are transferred from the extracorporeal part of the visual prosthesis to the stimulator chip of the intracorporeal part in the eye via the forth transmission channel (up-link). Such stimulation instructions may comprise the following information:
  electrode addresses, i.e. the addresses of the electrodes arranged in the electrode array which are used to stimulate the ganglion cells in the retina of the eye,
  current amplitudes, i.e. the information for the stimulator chip which specifies the current strength of the stimulation impulses to be generated,
  phase duration, i.e. the information for the stimulator chip which contains the phase duration of the stimulation impulses to be generated,
  phase ratio, i.e. the information for the stimulator chip which specifies the phase ratio of the stimulation impulses to be generated,
  polarity sign of the stimulation impulses, i.e. the information for the stimulator chip which contains the polarity sign of the stimulation impulses to be generated.

Measurement instructions, for example, may furthermore be transferred via the forth transmission channel (up-link) from the extracorporeal part of the visual prosthesis to the intracorporeal part. Measurement instructions are instructions from the extracorporeal part of the visual prosthesis to the intracorporeal part, to carry out particular measurements and transfer the ascertained measurement value via the back transmission channel (down-link) to the extracorporeal part of the visual prosthesis. Such measurement instructions may comprise the following information:
  voltage measurement on an electrode during the stimulation,
  voltage measurement on an electrode outside the stimulation,
  measurement of nerve action potentials with the aid of one or more stimulation electrodes,
  measurement of nerve action potentials with the aid of special measurement electrodes.

Status instructions, for example, may furthermore be transferred via the forth transmission channel (up-link) from the extracorporeal part to the intracorporeal part of the visual prosthesis. Such status instructions contain requests for the intracorporeal part of the visual prosthesis to record particular status parameters and transfer them via the back transmission channel (down-link) to the extracorporeal part of the visual prosthesis. The status instructions may, for example, contain requests for the intracorporeal part of the visual prosthesis to record the following status parameters and transfer them on the back transmission channel (down-link) to the extracorporeal part of the visual prosthesis:
  the identification number (ID number) of the implant,
  a status report of the implant, for example
    about the status of the charge balancing systems or
    about the status of the energy supply of the implant, i.e. for example whether it has too much energy or too little energy,
  the temperature of the stimulation chip or of implant parts,
  the moisture sensor measurement value.

According to another preferred embodiment of the visual prosthesis according to the invention, at least the forth transmission channel (up-link) from the extracorporeal part to the intracorporeal part of the visual prosthesis is configured in the form of optical data transmission. The data may in this case be transmitted via light signals by means of light-emitting diodes (LEDs) or by means of lasers, for example with infrared light. The natural light path of the eye may be used at least partially for the optical data transmission, by the light signals of the light-emitting diodes or the laser outside the eye being directed through the lens aperture of the eye onto an optical reception element inside the eye.

The data transmission between the intracorporeal part and the extracorporeal part of the visual prosthesis may be carried out with any desired coding on the back transmission channel (down-link). Balanced coding, which contains approximately the same number of zero-states and one-states, is preferably used so as to avoid driving the optical reception element to saturation. For example Manchester coding, so-called 4 PPM coding, 4 PPM+coding or other suitable coding methods may be used.

According to another preferred embodiment of the visual prosthesis according to the invention, the forth transmission channel (up link) and/or back transmission channel (down-link) between the intracorporeal part and the extracorporeal part of the visual prosthesis is configured in the form of electromagnetic data transmission, in which the carrier frequency of the transmitter is correspondingly modulated in order to transmit data. The electromagnetic data transmission may in this case be designed actively, in which case for example the 13.56 MHz ISM frequency band, the 27.12 MHz ISM frequency band, the 125 kHz ISM frequency band or another suitable frequency band is used as the carrier frequency of the transmitter. Instead of frequency modulation for the electromagnetic data transmission between the intracorporeal part and the extracorporeal part of the visual prosthesis, it is also possible to use amplitude modulation, phase modulation of the carrier frequency or other suitable modulation methods.

According to another modulation method which may be used for the visual prosthesis according to the invention, a separate data carrier frequency is used, for example in the 433 MHz ISM frequency band or in another suitable frequency range, which is preferably different to from the frequency for the energy input via the inductive interface. This separate data carrier frequency may in turn be modulated by one of the following methods:
  amplitude modulation of the data carrier frequency,
  frequency modulation of the data carrier frequency,
  phase modulation of the data carrier frequency,
  other suitable modulation methods.

Various types of data may be transmitted via the back transmission channel (down-link) from the intracorporeal part to the extracorporeal part of the visual prosthesis. In particular, diagnostic data about the status of the intracorporeal part of the visual prosthesis or about the status of the implant may be transferred via the back transmission channel (down-link), for example:
  measurement values for the electrode impedance of particular stimulation electrodes, measurement values for the electrical voltage which is applied to stimulation electrodes, monitoring data of the status of particular stimulation electrodes.

Information or diagnostic data about the system status of the process control in the intracorporeal part of the visual prosthesis or in the implant may also be transferred via the back transmission channel (down-link), for example information about the following control details:

data correctly transferred from the extracorporeal part to the intracorporeal part of the visual prosthesis (yes or no), intracorporeal part or implant correctly initialised (yes or no), system status reset carried out (yes or no), status of the energy supply of the implant (power status), for example status of the analogue component or components of the stimulator chip, send status of the so-called power-down stage of the intracorporeal part to the extracorporeal part of the visual prosthesis, fault in the stimulation of the retina of the eye, for example maximum stimulation current reached, charge balance between stimulation electrodes not achieved, charge balance between stimulation electrodes takes too long, stimulation was carried out even though not requested, for example owing to a fault in the output stage of a current source, status of the electrical energy supply, for example operating voltage too low, operating voltage too high, voltage on stimulation electrodes at particular measurement times.

Diagnostic data about the patient's physiology, for example reading of the action potentials of individual nerve cells, in particular ganglion cells, reading of the sum action potentials of nerve cells, in particular ganglion cells, so that information can be inferred about the stimulability of the contacted nerve cells diagnostic data about the general status of the intracorporeal part of the visual processes or the implant, for example temperature in the region of the electronics of the implant, temperature at a particular point in the eye, temperature at a plurality of positions in the eye, measurement value for the internal eye pressure, acceleration measurement of the implant, moisture measurement inside the housing of the implant.

As already described in conjunction with the forth transmission channel (up-link), the back transmission channel (down-link) from the intracorporeal part to the extracorporeal part of the visual prosthesis may also be designed as an optical data transmission path. To this end, as in the case of the forth transmission channel (up-link), the data may also be transmitted using light signals in the back transmission channel (down-link) by means of light-emitting diodes (LEDs) or by means of lasers, for example with infrared light. The natural light path of the eye may likewise be used at least partially in this case, by the light signals of a light-emitting element arranged inside the eye being directed through the lens aperture of the eye onto an optical reception element outside the eye. The optical reception element records the encoded light signals of the light-emitting element and forwards them in the form of electrical signals to electronics for evaluation.

According to another preferred embodiment of the visual prosthesis according to the invention, the back transmission channel (down-link) from the intracorporeal part to the extracorporeal part of the visual prosthesis is configured in the form of passive electromagnetic data transmission, in which the carrier frequency of a transmitter is correspondingly modulated in order to transmit data. For example, load modulation of the energy transmission frequency may be carried out as a modulation method in this case. The load modulation of the carrier frequency may be carried out by connecting and disconnecting a resistive load, a capacitive load or an inductive load according to the data stream to be transmitted. A combination or partial combination of the said methods is also possible for the electromagnetic data transmission between the intracorporeal part and the extracorporeal part of the visual prosthesis.

In addition or as an alternative, the data transmission via the back transmission channel (down-link) from the intracorporeal part (in the eye) to the extracorporeal part (for example in the spectacles) of the visual prosthesis according to the invention may be carried out by using an error correction method. Likewise, in addition or as an alternative, the data transmission via the forth transmission channel (up-link) from the extracorporeal part (in the spectacles) to the intracorporeal part of the visual prosthesis (in the eye) may be carried out by using an error correction method.

For example, a method which can recorrect a defined number of incorrectly transmitted data bits out of the data bits transmitted overall, by redundancy in the coding of the data transmission, may be used as an error correction method. One of the following methods may be used as an error correction method both for the forth transmission channel (up-link) and for the back transmission channel (down-link):

Hamming coding, convolution coding, repetition coding or other suitable error correction methods.

In addition or as an alternative to using an error correction method, the data transmission via the forth transmission channel (up-link) from the extracorporeal part (in the spectacles) to the intracorporeal part of the visual prosthesis (in the eye) may be also carried out by using an error detection method. Likewise, in addition or as an alternative, the data transmission via the back transmission channel (down-link) from the intracorporeal part (in the eye) to the extracorporeal part (in the spectacles) of the visual prosthesis according to the invention may likewise be carried out by using an error detection method. Such an error detection method may be implemented by various coding methods, for example:

cyclic redundancy check (CRC) coding, parity check coding, repetition coding or other suitable error detection methods.

A data rate in the range of from 100 kilobits/second to 10 megabits/second, preferably a data rate in the range of from 1 megabit/second to 10 megabits/second, particularly preferably from 1 to 5 megabits/second and even more preferably from 1 to 2 megabits/second, may be used for the data transmission via the forth transmission channel (up-link) from the extracorporeal part (in the spectacles) to the intracorporeal part (in the eye) of the visual prosthesis according to the invention.

A data rate in the range of from 1 kilobit/second to 100 kilobits/second, preferably a data rate in the range of from 5 to 20 kilobits/second, may be used for the data transmission via the back transmission channel (down-link) from the intracorporeal part (in the eye) to the extracorporeal part (in the spectacles) of the visual prosthesis according to the invention. The data rates used for the data transmission via the forth transmission channel (up-link) and for the data transmission via the back transmission channel (down-link) may in this case be different.

Further details, preferred embodiments and advantages of the present invention will be found in the following description with reference to the drawing, in which:

DETAILED DESCRIPTION OF THE DISCLOSURE

Figure 1:
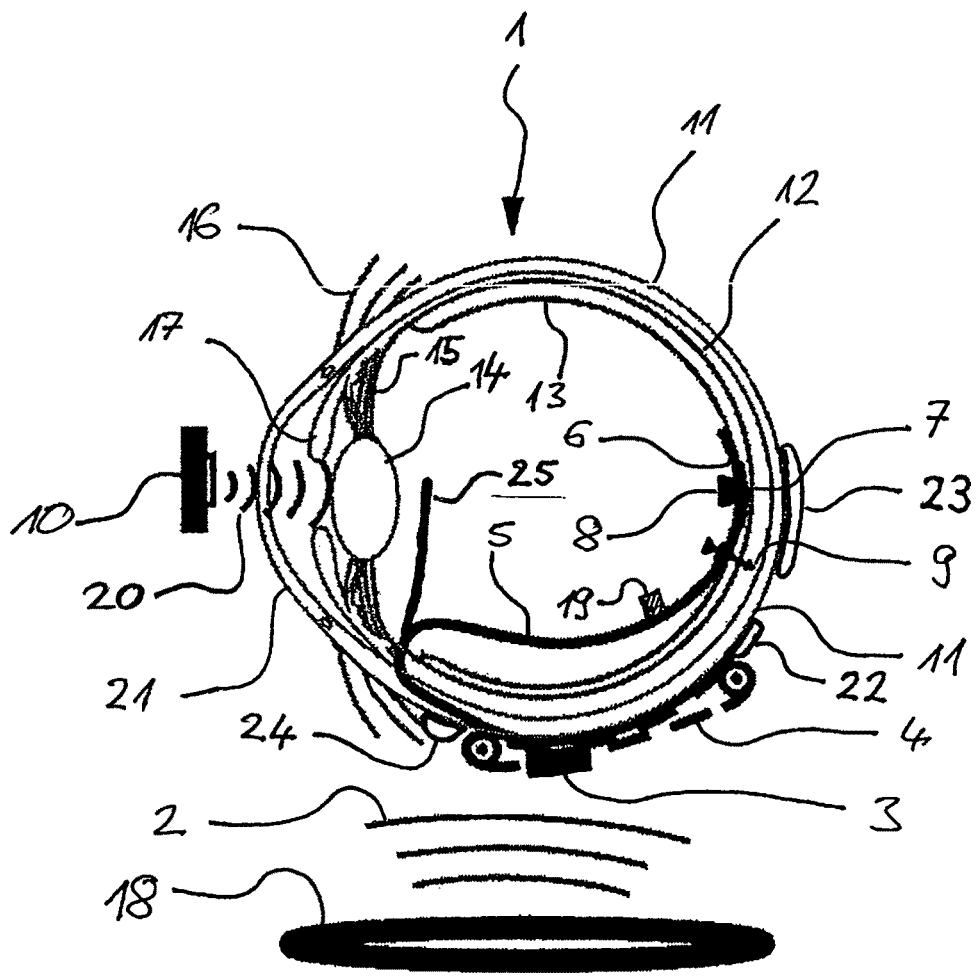
FIG. 1 shows a schematic representation of the cross section through a human eye with a visual prosthesis according to a preferred embodiment of the present invention.

FIG. 1 shows a schematic representation in cross section through a human eye with a visual prosthesis according to a preferred embodiment of the present invention. The eyeball 1 of the human eye has an essentially round shape, the transparent cornea 21 having a more pronounced curvature on its anterior side. The region of the eyeball 1 held in the eye socket is constructed from a plurality of layers, the outermost layer constituting the so-called sclera 11. The sclera 11 is followed in the direction of the interior of the eye by the choroid 12, on which the so-called retina 13 with photosensitive cells or photoreceptors (cones, rods and ganglion cells) rests.

In a healthy human eye, the natural light path travels via the transparent cornea 21 in the anterior region of the eyeball 1 through the iris 17 and the biconvex lens 14, the shape or refractive energy of which can be modified by tensioning the ciliary muscle 15. The incident light enters the interior of the eye while being optically refracted by the cornea 21 and the eye lens 14, and is projected onto the retina 13 in the posterior region of the eyeball 1. The light-sensitive photoreceptors in the retina 13 convert the image of the incident light projected onto the retina into nerve signals, which are forwarded to the brain by the ganglion cells in the retina (not shown).

The purpose of the visual prosthesis according to the invention is to restore or improve a visual process impaired or destroyed owing to degenerative modifications on the retina 13. A prerequisite for using the visual prosthesis according to the invention is that the ganglion cells contained in the retina 13 are substantially intact and are capable of forwarding nerve impulses via the optic nerve to the brain.

According to the preferred embodiment represented in FIG. 1, the visual prosthesis according to the invention comprises a stimulation system with an intraocular implant 6, 8, which is arranged inside the eyeball 1, and an extraocular implant 3, 4 which is arranged outside the eyeball 1. The intraocular implant is designed as an epiretinal implant, i.e. the intraocular implant is arranged on the retina 13 in the posterior region of the eye as seen from inside the eye.

The intraocular implant is coupled to the extraocular implant a via a wire connection 5. The wire connection 5 is designed as a flexible implant, which extends from the extraocular implant outside the eyeball 1, directly behind the connective tissue 16 in the region of the so-called pars plana between the ciliary muscle 15 and the retina 13 into the interior of the eye and to the intraocular implant. The wire connection 5 comprises electrical lines in order to provide the current supply of the intraocular implant via the extraocular implant. The wire connection 5 furthermore comprises electrical lines in a sufficient number to allow transfer of image data or diagnostic instructions, control instructions or stimulation instructions in the form of serial data streams and/or parallel data streams or signal streams between the intraocular implant and the extraocular implant.

The intraocular implant comprises an electrode array 6, which bears epiretinally on the retina 13 and has a number of stimulation electrodes, for example arranged in a matrix. The stimulation electrodes of the electrode array 6 are connected to ganglion cells and can stimulate them by means of stimulation impulses or stimulation currents. The electrode array 6 of the epiretinal implant is centred in the region of the macula of the eye, where the greatest amount of light arrives on the retina 13 via the natural light path. In order to ensure a secure position of the intraocular implant on the retina, it is fastened inside the eye with the aid of a so-called nail or tack 9 which extends through the intraocular implant and the retina 13 and is anchored by retaining hooks in the sclera 11.

An infrared receiver 8, which can receive light signals from an infrared transmitter 10 outside the eye via the natural light path, is arranged on the intraocular implant. An image is captured by an external camera (not shown), and its preprocessed image data are transferred via the infrared transmitter 10 along the natural light path of the human eye to the infrared receiver 8 of the intraocular implant. These image data are forwarded from the intraocular implant to the extraocular implant via the wire connection 5, preferably in the form of the serial data stream.

Any position along the wire connection 5 is conceivable for the infrared receiver 8, although it preferably lies in the region of the nail or tack 9. As an alternative, the infrared receiver 8 may lie on a branch 25 of the wire connection 5 in order to adjust the reception properties favourably. This branch 25 departs from the wire connection 5 and expediently protrudes into the eye in the beam path of the natural light path. In this way, the infrared signals incident in the eye via the natural light path from outside the eye can arrive directly on the infrared receiver 8 arranged on the branch 25 of the wire connection 5.

The image data are evaluated in the retinal stimulator chip 3 of the extraocular implant and converted into the stimulation impulses or stimulation currents. The stimulation impulses or stimulation currents are subsequently transferred in the form of a parallel signal stream via the wire connection 5 to the stimulation electrodes in the electrode array 6 of the intraocular implant, and flow back via the counter-electrode 22, 23 and/or 24 into the respective current source. The stimulation electrodes stimulate the ganglion cells in the retina via the microcontact structure according to the position-resolved stimulation impulses, and thereby generate a visual impression with nerve signals, which corresponds to the image captured by the external camera.

The stimulation system of the visual prosthesis according to the invention furthermore comprises an extraocular implant, which is arranged outside the eyeball 1 on the sclera 11. All those components of the stimulation system which do not necessarily need to be arranged on the intraocular implant inside the eye are accommodated in the extraocular implant. The extraocular implant comprises a retinal stimulator chip 3, which can calculate and generate stimulation impulses or stimulation currents for the stimulation electrodes of the intraocular implant on the basis of received image data. To this end, the retinal stimulator chip 3 comprises electronic components for calculating the intensity and duration of the stimulation impulses with the aid of the received image data, current generators for generating the required stimulation currents and electronic storage means, in which the parameters of the stimulation impulses and the coordinates of the corresponding stimulation electrodes are buffered and can be called up or released in response to a particular command.

The extraocular implant furthermore comprises at least one counter-electrode which, for example, may be arranged in the positions which are denoted by the references 22, 23 and 24 in FIG. 1. The counter-electrodes 22, 23, 24 are used as a return current path for the stimulation current sources, in order to close the current path to the stimulation electrodes in the electrode array 6 via the tissue of the sclera 11, choroid 12 and the retina 13.

The extraocular implant furthermore comprises a radiofrequency antenna 4, via which radiofrequency signals 2 that are emitted by a radiofrequency antenna 18 arranged remotely from the eyeball 1 can be received. Via the inductive interface between the radiofrequency antenna 4 of the extraocular implant and the external radiofrequency antenna 18, inductive energy which is required for operation of the extraocular implant and the intraocular implant can be transferred.

The external radiofrequency antenna 18 may, for example, be accommodated together with other electronic components outside the body in an extracorporeal part of the visual prosthesis according to the invention, for example in spectacles which the patient may wear like a normal visual aid. Conversely, the intraocular implant 6, 8 and the extraocular implant 3, 4 constitutes an intracorporeal part 3, 4, 6, 8 of the visual prosthesis according to the invention. Via the inductive interlace, wireless contact can be established between the extracorporeal part and the intracorporeal part of the visual prosthesis according to the invention.

Via this inductive interface between the extracorporeal part and the intracorporeal part, the image data captured by an external camera can also be transferred to the retinal stimulator chip 3 which generates stimulation impulses with the aid of the received image data and forwards them via the wire connection 5 to the stimulation electrodes in the intraocular implant. The inductive interface between the radiofrequency antenna of the intraocular implant and the external radiofrequency antenna 18 may also be designed bidirectionally, so that the retina stimulation chip 3 can transfer information about operating parameters of the intraocular implant and/or the extraocular implant inductively via the radiofrequency antenna 4 to the external radiofrequency antenna 18, and these may then be evaluated by external electronics (not shown).

In order to set up the bidirectional inductive interface between the extracorporeal part and the intracorporeal part of the visual prosthesis according to the invention, the extracorporeal part outside the eye 1 may have an antenna 18 which can both transmit and receive electromagnetic signals 2, preferably in the radiofrequency range. The extraocular implant 3, 4 and/or the intraocular implant 6, 8 may likewise have an antenna 4 which can both transmit and receive electromagnetic signals 2, preferably in the radiofrequency range.

As an alternative, the extracorporeal part of the visual prosthesis according to the invention may comprise at least two antennas 18 for the bidirectional inductive interface, of which a first antenna can transmit electromagnetic signals 2 and a second antenna can receive electromagnetic signals 2. The extracorporeal part of the visual prosthesis according to the invention, i.e. the extraocular implant 3, 4 and/or the intraocular implant 6, 8, may comprise at least two antennas 4 for the bidirectional inductive interface, of which a first antenna can transmit electromagnetic signals 2 and a second antenna can receive electromagnetic signals 2.

The intraocular implant furthermore comprises a light-emitting element 19, which generates light signals as a function of operating parameters of the intraocular implant. This light-emitting element 19 is designed for example as an infrared diode, the infrared light signals of which can be perceived by an observer or a corresponding infrared receiver outside the eye. With the aid of the light signals emitted by the light-emitting element 19, for example, it is possible to establish the optimal position of the intraocular implant on the retina 13 during the operative implantation. The light-emitting element 19 may therefore also be referred to as a status display. Any position of the light-emitting element 19 over the region of the wire connection 5 is conceivable, although it preferably lies in the region of the nail or tack 9. As an alternative, the light-emitting element 19 may also lie on the branch 25 of the wire connection 5 in order to adjust the emission properties favourably.

For the transmission of information, the electromagnetic signals 2 may be encoded during the data transmission via the bidirectional inductive interface and the light signals may be encoded during the data transmission via the optical interface, by using one of the methods described above. One of the error correction and error detection methods described above may also be employed in this case.

The present invention achieves the aforementioned object by a visual prosthesis with an epiretinal implant, which is supplied with current via an extraocular device, the extraocular device receiving the current from a radiofrequency transmitter via an inductive interface and therefore wirelessly. The radiofrequency transmitter may be arranged inside or in the vicinity of the eye socket, for example in spectacles, or remotely from the human eye provided with the implant.

The present invention furthermore achieves the aforementioned object by a bidirectional inductive interface between a transmitter/receiver or antenna arranged outside the eye and the body, and a transmitter/receiver or antenna arranged inside the body, on or in the eye, via which bidirectional data transmission can be carried out between the extracorporeal part and the intracorporeal part of the visual prosthesis.

Figure 2:
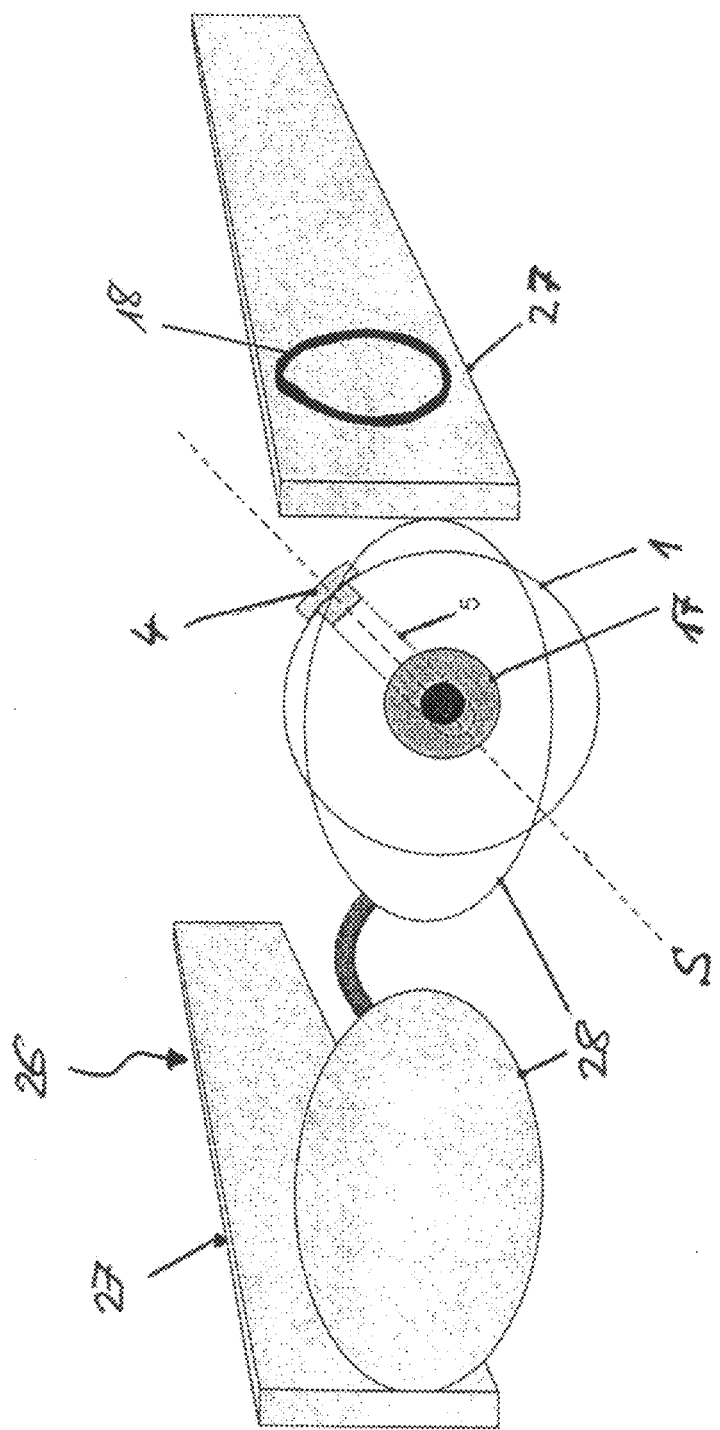
FIG. 2 shows a perspective view of a stimulation system comprising spectacles and a human eye with a visual prosthesis according to the invention.

FIG. 2 shows a perspective view of a stimulation system comprising spectacles and a human eye with a visual prosthesis according to the invention. In the stimulation system represented in FIG. 2, the extracorporeal components of the visual prosthesis according to the invention are accommodated in spectacles or a spectacle frame 26, which the patient may wear like conventional spectacles. The spectacles 26 comprise two spectacle side-arms 27 for arranging the spectacles 26 conventionally on the patient's head, and two spectacle lens holders 28 for receiving spectacle lenses, which may be without an optical function and serve merely for the natural appearance of the spectacles.

The spectacle side-arms 27 may for example accommodate the external camera, in particular a video camera (not shown), which captures the image or successive sequences of images in front of the patient's field of view. Electronic components of the visual prosthesis, which are needed for processing and preparing the image data captured by the external camera, may likewise be accommodated in the spectacles or in the spectacle frame 26. As an alternative or in addition, electronic components of the visual prosthesis may be accommodated in a so-called pocket computer, which the patient may carry in a separate pocket on their body.

The spectacles 26, in particular the spectacle side-arms 27, may also accommodate the receiver coil and the transmitter coil 18 of the extracorporeal part of the visual prosthesis, which can respectively transmit and receive electromagnetic signals preferably in the radiofrequency range. The inductive interface between the extracorporeal part and the intracorporeal part of the visual prosthesis is formed bidirectionally owing to the transmission and reception functions of the transmitter and receiver coil 18 in the spectacles and the transmitter and receiver coil 4 of the extraocular intracorporeal part of the visual prosthesis. The receiver coil and/or the transmitter coil 18 or the transmitter/receiver coil of the extracorporeal part of the visual prosthesis are advantageously accommodated in the spectacle lens holder 28, for example by the loop of the spectacle lens holder 28 constituting the coil per se.

In the embodiment of the stimulation system according to the invention as represented in FIG. 2, an image is initially captured during operation by the external camera in the spectacles 26, the image signals of which are transferred inductively after electronic preprocessing via the transmitter and receiver coil 18 in the spectacle side-arm 27 to the transmitter and receiver coil 4 of the intracorporeal part, and are forwarded from there via the wire connection 5 to the epiretinal electrode array 8 of the intraocular implant. The electrode array 8 stimulates the cells of the retina by electrical signals according to the received image data, and thus forwards the image captured by the external camera to the nerves of the visual system. In this way, the image captured by the camera is converted into electrical signals, transmitted from the extracorporeal part via the bidirectional inductive interface to the intracorporeal part of the visual prosthesis, and delivered via stimulation electrodes by means of electrical stimulation impulses to the ganglion cells of the retina, or to the optic nerve, so as to restore or improve the eyesight of a visually handicapped patient.

Figure 3:
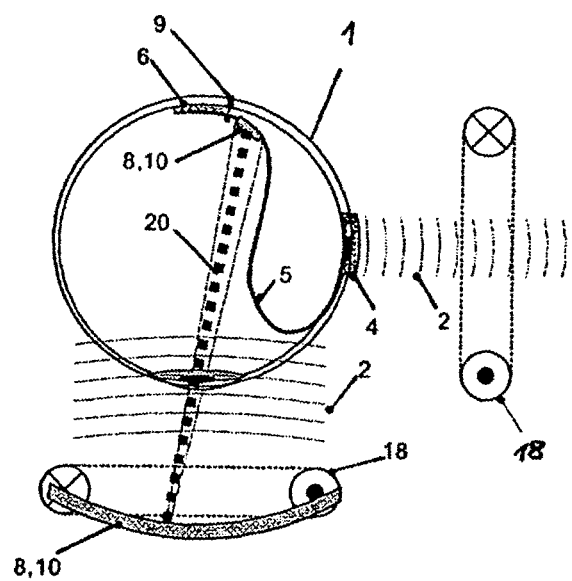
FIG. 3 shows a schematic representation of the cross section through a human eye with a visual prosthesis according to a second preferred embodiment of the present invention.

FIG. 2 also shows a dashed line S, which extends centrally through the eye 1 and represents the section plane of FIGS. 3 to 6. FIG. 3 shows a schematic representation of the cross section, along the section plane S shown in FIG. 2, through a human eye with a visual prosthesis according to a second preferred embodiment of the present invention. In this second preferred embodiment of the visual prosthesis according to the invention, the intraocular part comprises the electrode array or microcontact structure 6, the nail or tack 9 for epiretinal fastening, the infrared receiver 8 and the wire connection 5 between the intraocular part and the extraocular components of the visual prosthesis. A transmitter/receiver coil 4, which can both transmit and receive electromagnetic waves 2, is represented as an extraocular intracorporeal component of the visual prosthesis.

Arranged below the eye 1, there is a transmitter coil 18 which lies outside the body and transfers signals inductively to the transmitter/receiver coil 4 via electromagnetic waves 2, preferably in the radiofrequency range. The signals received by the extraocular transmitter/receiver coil 4 are then forwarded via the wire connection 5 to the intraocular part of the visual prosthesis, as described above. Arranged on the right-hand side of the eye, there is a receiver coil 18 which also lies outside the body and inductively receives the electromagnetic signals 2 emitted by the extraocular transmitter/receiver coil 4. In this way, signals or data can be transferred inductively from outside the eye 1 to the intraocular part of the visual prosthesis and, in the other direction, signals or data can be transmitted inductively in parallel from inside the eye 1 to the extracorporeal part of the visual prosthesis, as described above.

An infrared transmitter/receiver 8, 10 may also be provided inside the eye 1, which transfers data from the intraocular part of the visual prosthesis by infrared signals 20 that radiate outwards via the natural light path of the eye through the pupil and are recorded by an infrared receiver 8 arranged outside the body. The extracorporeal infrared receiver 8 may also have the function of an infrared transmitter, or an infrared transmitter 10 separate from the infrared receiver 8 may be provided, which transfers data by infrared signals 20 that radiate from outside the body via the natural light path of the eye through the pupil into the eye, and are recorded by the infrared transmitter/receiver 8, 10 of the intraocular part of the visual prosthesis. In this way, signals or data can be transferred by means of infrared signals 20 from outside the eye 1 to the intraocular part of the visual prosthesis and, in the other direction, signals or data can be transmitted by means of infrared signals 20 from inside the eye 1 to the extracorporeal part of the visual prosthesis.

Figure 4:
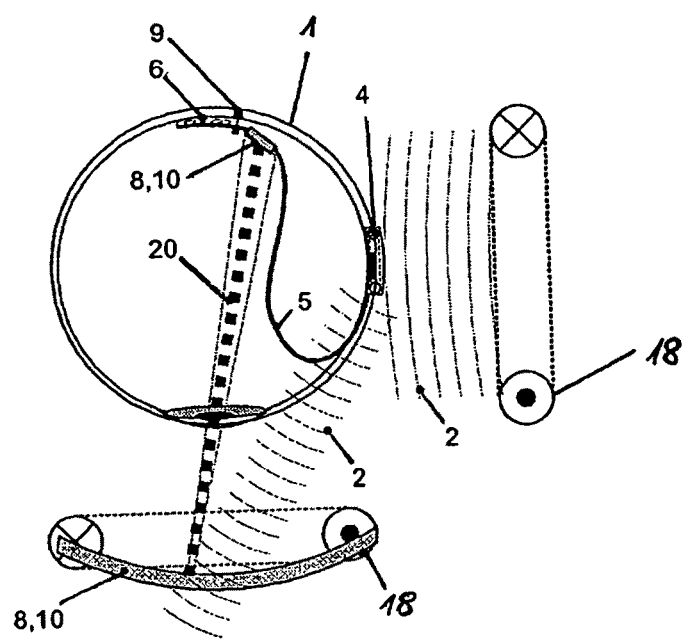
FIG. 4 shows a schematic representation of the cross section through a human eye with a visual prosthesis according to a third preferred embodiment of the present invention.

FIG. 4 shows a schematic representation of the cross section, along the section plane S shown in FIG. 2, through a human eye with a visual prosthesis according to a third preferred embodiment of the present invention. Like the embodiment shown in FIG. 3, this third preferred embodiment of the visual prosthesis according to the invention also comprises an intraocular part with an electrode array or microcontact structure 6, the nail or tack 9, the infrared transmitter/receiver 8, 10 and the wire connection 5 between the intraocular and extraocular parts of the visual prosthesis. A transmitter/receiver coil 4, which can both transmit and receive electromagnetic waves 2, is again represented as an extraocular component of the visual prosthesis.

In contrast to the visual prosthesis represented in FIG. 3, in the third embodiment shown in FIG. 4 arranged on the right-hand side of the eye there is a transmitter coil 18 which lies outside the body and transfers signals inductively to the intracorporeal transmitter/receiver coil 4 via electromagnetic waves 2. The signals received by the intracorporeal transmitter/receiver coil 4 are then forwarded via the wire connection 5 to the intraocular part of the visual prosthesis.

Arranged below the eye 1, there is a receiver coil 18 which also lies outside the body and inductively receives the electromagnetic signals 2 emitted by the extraocular transmitter/receiver coil 4. In this way, signals or data can be transferred inductively from outside the eye 1 to the intraocular part of the visual prosthesis and, in the other direction, signals or data can be transmitted inductively in parallel operation from inside the eye 1 to the extracorporeal part of the visual prosthesis, as described above.

As in the visual prosthesis represented in FIG. 3, in the third preferred embodiment as shown in FIG. 4 an infrared transmitter/receiver 8, 10 may also be provided inside the eye 1, which transfers data from the intraocular part of the visual prosthesis by infrared signals 20 that radiate outwards via the natural light path of the eye and are recorded by an infrared receiver 8 arranged outside the body. The extracorporeal infrared receiver 8 may also have the function of an infrared transmitter, or a separate infrared transmitter 10 may be provided further to the infrared receiver, which transfers data by infrared signals 20 that enter the eye from outside the body via the natural light path of the eye and are recorded there by the infrared transmitter/receiver 8, 10 of the intraocular part of the visual prosthesis. In this way, signals or data can be transferred by means of infrared signals 20 from outside the eye 1 to the intraocular part of the visual prosthesis and, in the other direction, signals or data can be transmitted by means of infrared signals 20 from inside the eye 1 to the extracorporeal part of the visual prosthesis.

Figure 5:
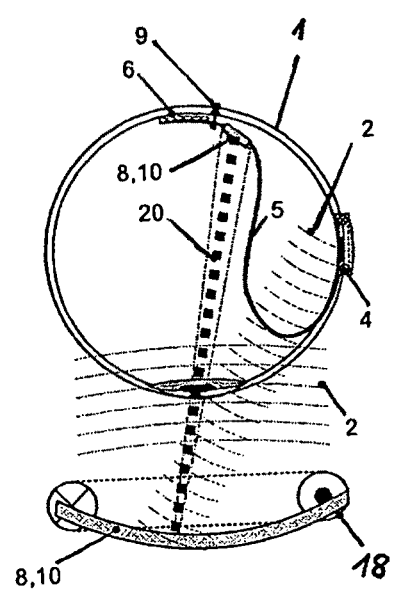
FIG. 5 shows a schematic representation of the cross section through a human eye with a visual prosthesis according to a fourth preferred embodiment of the present invention.

FIG. 5 shows a schematic representation of the cross section, along the section plane S shown in FIG. 2, through a human eye with a visual prosthesis according to a fourth preferred embodiment of the present invention. As in the embodiments described above, the electrode array 6, the nail or tack 9, the infrared transmitter/receiver 8, 10 and the wire connection 5 between the intraocular part and the extraocular components of the visual prosthesis are represented inside the eye 1 in this fourth preferred embodiment. The transmitter/receiver coil 4 is again arranged intracorporeally but outside the eye 1, and can both transmit and receive electromagnetic waves 2.

Arranged on the right hand side of the eye 1, there is a transmitter/receiver coil 18 which lies outside the body and, via electromagnetic waves 2, transfers signals inductively to the transmitter/receiver coil 4, which are forwarded from the extraocular part via the wire connection 5 to the intraocular part of the visual prosthesis. The signals received by the extraocular transmitter/receiver coil 4 are then forwarded via the wire connection 5 to the intraocular part of the visual prosthesis. In contrast to the embodiments described above, a separate receiver coil is not provided in this fourth preferred embodiment, but the transmitter/receiver coil 18 can both transmit and receive electromagnetic waves 2 like the extraocular transmitter/receiver coil 4. Via this bidirectional interface between the transmitter/receiver coil 4 and the transmitter/receiver coil 18, signals or data can be transferred inductively from outside the eye 1 to the intraocular part of the visual prosthesis and, in the other direction, signals or data can be transmitted inductively in an alternating operation mode from inside the eye 1 to the extracorporeal part of the visual prosthesis, as described above.

An infrared transmitter/receiver 8, 10 is also be provided inside the eye 1 in the fourth preferred embodiment as represented in FIG. 5, which transfers data from the intraocular part of the visual prosthesis by infrared signals 20 that radiate outwards via the natural light path of the eye and are recorded by an infrared receiver 8 arranged outside the body. The extracorporeal infrared transmitter/receiver 8, 10 may also have the function of an infrared transmitter, or a separate infrared transmitter 10 may be provided further to the infrared receiver, which transfers data by infrared signals 20 that that enter the eye from outside the body via the natural light path of the eye and are recorded by the infrared transmitter/receiver 8, 10 of the intraocular part of the visual prosthesis. In this way, signals or data can be transferred by means of infrared signals 20 from outside the eye 1 to the intraocular part of the visual prosthesis and, in the other direction, signals or data can be transmitted by means of infrared signals 20 from inside the eye 1 to the extracorporeal part of the visual prosthesis.

According to the embodiments shown in FIGS. 3, 4 and 5, the infrared transmitter/receiver 8, 10 and the extracorporeal transmitter/receiver coil 18 may be combined together in one device. The infrared transmitter/receiver 8, 10 preferably comprises a parabolic photosensitive surface, so that the infrared signals 20 travelling outwards from the intraocular infrared transmitter 10 via the natural light path of the eye 1 can be recorded reliably.

Figure 6:
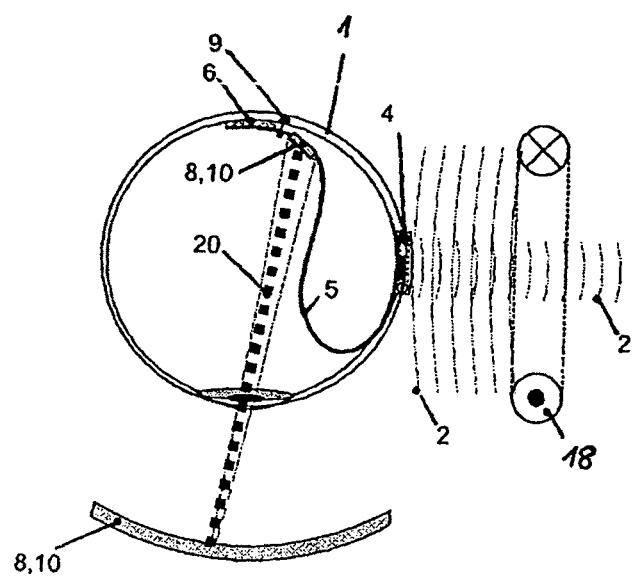
FIG. 6 shows a schematic representation of the cross section through a human eye with a visual prosthesis according to a fifth preferred embodiment of the present invention.

FIG. 6 shows a schematic representation of the cross section, along the section plane S shown in FIG. 2, through a human eye with a visual prosthesis according to a fifth preferred embodiment of the present invention. As in the embodiments described above, the electrode array 6, the nail or tack 9, the infrared transmitter/receiver 8, 10 and the wire connection 5 between the intraocular part and the extraocular components of the visual prosthesis are also arranged inside the eye 1 in this fifth preferred embodiment. The transmitter/receiver coil 4 is arranged intracorporeally but outside the eye 1, and can both transmit and receive electromagnetic waves 2.

Arranged on the right hand side of the eye 1, there is a transmitter/receiver coil 18 which lies outside the body and, via electromagnetic waves 2, transfers signals inductively to the transmitter/receiver coil 4, which are forwarded from the extraocular part via the wire connection 5 to the intraocular part of the visual prosthesis. Similarly as in the embodiments represented in FIG. 5, a separate receiver coil is likewise not provided in this fifth embodiment, but the extracorporeal transmitter/receiver coil 18 can both transmit and receive electromagnetic. waves 2 like the intracorporeal transmitter/receiver coil 4. Via this bidirectional interface between the transmitter/receiver coil 4 and the transmitter/receiver coil 18, signals or data can be transferred inductively from outside the eye 1 to the intraocular part of the visual prosthesis and, in the other direction, signals or data can be transmitted inductively in an alternating operation mode from inside the eye 1 to the extracorporeal part of the visual prosthesis, as described above.

An infrared transmitter/receiver 8, 10 is also be provided inside the eye 1 in the fifth preferred embodiment as represented in FIG. 6, which transfers data from the intraocular part of the visual prosthesis by infrared signals 20 that radiate outwards via the natural light path of the eye and are recorded by an infrared receiver 8 arranged outside the body. The extracorporeal infrared transmitter/receiver 8 also has the function of an infrared transmitter, which transfers data by infrared signals 20 that enter the eye from outside the body via the natural light path of the eye and are recorded by the infrared transmitter/receiver 8, 10 of the intraocular part of the visual prosthesis. In this way, signals or data can be transferred by means of infrared signals 20 from outside the eye 1 to the intraocular part of the visual prosthesis and, in the other direction, signals or data can be transmitted by means of infrared signals 20 from inside the eye 1 to the extracorporeal part of the visual prosthesis.

In contrast to the embodiments represented in FIGS. 3, 4 and 5, the infrared transmitter/receiver 8, 10 and the extracorporeal transmitter/receiver coil 18 are not combined together in one device in this fifth embodiment as shown in FIG. 6, but they are arranged separately from one another. The infrared transmitter/receiver 8, 10 again comprises a parabolic surface with photosensitive sensors, so that the infrared signals 20 travelling outwards from the intraocular infrared transmitter 10 via the natural light path of the eye 1 can be recorded reliably.

LIST OF REFERENCES

1 human eye or eyeball
2 electromagnetic radiofrequency signals
3 retinal stimulator chip or RS chip
4 radiofrequency transmitter/receiver coil
5 wire connection between RS chip 3 and electrode array 6

6 electrode array or microcontact structure
7 macula or place of sharpest vision
8 infrared receiver
9 nail or tack
10 infrared transmitter
11 sclera
12 choroid
13 retina
14 eye lens
15 ciliary muscle
16 connective tissue
17 iris
18 radiofrequency transmitter/receiver coil
19 light-emitting element or infrared diode
20 infrared signals
21 cornea
22 counter-electrode
23 counter-electrode
24 counter-electrode
25 branch of the wire connection 5
26 spectacles or spectacle frame
27 spectacle side-arm
28 spectacle lens holder
S section plane

The invention claimed is:

1. A visual prosthesis for implantation in a human eye, the visual prosthesis comprising:
a stimulation system comprising:
an intraocular implant part configured to be attached to an inside of the eye, wherein the intraocular implant part includes an electrode array having a number of stimulating electrodes for contacting and stimulating living tissue or nerves in a visual system of the eye; and
an extraocular implant part configured to be attached to an outside of the eye, wherein the extraocular implant part includes an electrical control unit, wherein the extraocular implant part supplies the intraocular implant part with energy, and
wherein the electrical control unit generates electrical stimulation impulses,
wherein the electrical control unit comprises:
a current/voltage source; and
an impulse generator that is adapted to generate the electrical stimulation impulses wherein the electrical stimulation impulses represent image data;
wherein the extraocular implant part comprises at least one counter-electrode that is connected to the current/voltage source, arranged outside of the eye and configured to be attached to the eye,
wherein the current/voltage source is adapted to amplify the electrical stimulation impulses generated by the impulse generator and to forward the electrical stimulation impulses to the number of stimulation electrodes in the electrode array,
wherein the number of stimulation electrodes in the electrode array and the at least one counter-electrode are arranged such that the electrical stimulation impulses forwarded to the number of stimulation electrodes flow back through the at least one counter-electrode via tissue of the eye into the current/voltage source.

2. The visual prosthesis according to claim 1, further comprising a bidirectional inductive interface for bidirectional data transmission, with at least two separate transmission channels, between an extracorporeal part of the visual prosthesis and an intracorporeal part which comprises the intraocular implant part and the extraocular implant part.

3. The visual prosthesis according to claim 1, further comprising an extracorporeal part, wherein the extracorporeal part comprises an antenna outside the eye for a bidirectional inductive interface, which can transmit and receive electromagnetic signals in a radiofrequency range.

4. The visual prosthesis according to claim 3, wherein the bidirectional inductive interface between the antenna of the extracorporeal part outside the eye and an antenna of an intracorporeal part is designed to transfer image data captured by an external camera via electromagnetic signals from the antenna outside the eye to an antenna of the extraocular implant part.

5. The visual prosthesis according to claim 1, wherein the extraocular implant part and the intraocular implant part each comprises an antenna for a bidirectional inductive interface, which can transmit and receive electromagnetic signals in a radiofrequency range.

6. The visual prosthesis according to claim 5, wherein a bidirectional inductive interface between an antenna of an extracorporeal part outside the eye and the antenna of the extraocular implant part is configured to transfer electrical energy, which is required for operation of the extraocular implant part and the intraocular implant part, inductively from the antenna of the extracorporeal part outside the eye to the antenna of the extraocular implant part.

7. The visual prosthesis according to claim 5, wherein a data rate of signals received by the antenna of the extraocular implant part is different from a data rate of the signals transmitted by the antenna of the extraocular implant part.

8. The visual prosthesis according to claim 5, wherein the bidirectional inductive interface is designed between an antenna of an extracorporeal part outside the eye and the antenna of the extraocular implant part, and the extraocular implant part is designed, to transfer information about the status and/or about operating parameters of an intracorporeal part via the inductive interface to the extracorporeal part.

9. The visual prosthesis according to claim 5, further comprising an extracorporeal part including an antenna accommodated in a spectacle frame.

10. The visual prosthesis according to claim 5, further comprising an extracorporeal part including an infrared receiver that has a parabolic photosensitive surface, in order to receive signals emitted by an intraocular infrared transmitter.

11. The visual prosthesis according to claim 1, wherein an extracorporeal part comprises at least two antennas for a bidirectional inductive interface, of which a first antenna can transmit electromagnetic signals and a second antenna can receive electromagnetic signals.

12. The visual prosthesis according to claim 1, wherein the extraocular implant part and/or the intraocular implant part comprises at least two antennas for a bidirectional inductive interface, of which a first antenna can transmit electromagnetic signals and a second antenna can receive electromagnetic signals.

13. The visual prosthesis according to claim 1, wherein the intraocular implant part is designed as an epiretinal implant, which is suitable for implantation inside the eye on the retina of the eye, in a region of a macula.

14. The visual prosthesis according to claim 1, wherein the extraocular implant part is suitable fixing on the sclera of the eye.

15. The visual prosthesis according to claim 1, wherein the stimulating electrodes of the electrode array are arranged in a matrix.

16. The visual prosthesis according to claim 15, wherein the electrode array of the intraocular implant part has a number of contact sites for contacting retinal cells or ganglion cells, via which contacted retinal cells or ganglion cells can be stimulated by means of the electrical stimulation impulses.

17. The visual prosthesis according to claim 1, wherein the extraocular implant part is designed as a digital control unit with analogue auxiliary functions.

18. The visual prosthesis according to claim 1, wherein electrical control unit comprises electronic storage means, in order to store therein the a duration and an intensity of the electrical stimulation impulses to be generated.

19. The visual prosthesis according to claim 1, wherein electronic components of the electrical control unit are accommodated at least partially in an integrated circuit, by being photolithographically microstructured, and on a chip in the extraocular implant part.

20. The visual prosthesis according to claim 1, wherein the electrical control unit comprises a contact pad for a stimulation electrode, for respectively contacting the stimulation electrode via a separate wire connection.

21. The visual prosthesis according to claim 20, wherein a wire connection between the extraocular implant part and the intraocular implant part comprises at least as many lines for transmitting electrical stimulation impulses as there are stimulation electrodes in the intraocular implant part.

22. The visual prosthesis according to claim 20, wherein the wire connection furthermore comprises one or more optical fibers, for bidirectional data transmission by means of light signals between the extraocular implant part and the intraocular implant part.

23. The visual prosthesis according to claim 20, wherein a wire connection between the extraocular implant part and the intraocular implant part is configured as a flexible implant and is configured to be fed from outside the eyeball into the interior of the eye in a region of a pars plana.

24. The visual prosthesis according to claim 1, wherein the extraocular implant part can be coupled to the intraocular implant part via a wire connection, which comprises at least one line for transmitting an operating current and at least one signal line for transmitting electrical stimulation impulses from a digital control unit to the intraocular implant part.

25. The visual prosthesis according to claim 1, wherein the intraocular implant part comprises a number of photosensitive elements, which drive the contact sites of the electrode array via the electrical circuit as a function of light incident on the intraocular implant part.

26. The visual prosthesis according to claim 1, wherein the intraocular implant part comprises at least one light receiver, which is designed to receive light signals of a light transmitter from outside the eye, via the natural light path of the eye.

27. The visual prosthesis according to claim 26, wherein the at least one light receiver of the intraocular implant part is designed as an infrared receiver, to receive infrared signals of an infrared transmitter from outside the eye, via the natural light path of the eye.

28. The visual prosthesis according to claim 26, wherein an interface between the light transmitter outside the eye and photosensitive elements or the at least one light receiver of the intraocular implant part is designed to transfer image data captured by an external camera via light signals from the light transmitter outside the eye to the photosensitive elements or the at least one light receiver of intraocular implant part.

29. The visual prosthesis according to claim 26, wherein the at least one light receiver and an electrical circuit can be coupled via a wire connection which is used to transmit image data, in the form of a serial data stream.

30. The visual prosthesis according to claim 29, wherein the at least one light receiver is positioned on the wire connection, in a region of a nail or tack used for fixing the wire connection or on a branch of the wire connection.

31. The visual prosthesis according to claim 26, further comprising an infrared transmitter and/or an infrared receiver and an extracorporeal part including an antenna, wherein the infrared transmitter and/or the infrared receiver and the antenna of the extracorporeal part are accommodated together in one device.

32. The visual prosthesis according to claim 1, wherein the intraocular implant part comprises at least one light-emitting element, which radiates light signals as a function of operating parameters of the stimulation system.

33. The visual prosthesis according to claim 32, wherein the at least one light-emitting element is positioned on a wire connection, in a region of a nail or tack used for fixing the wire connection or on a branch of the wire connection.

34. The visual prosthesis according to claim 32, wherein the light signals emitted by the at least one light-emitting element are modulated as a function of operating parameters of the intraocular implant part, by modulating a duration and/or an intensity of the light signals.

35. The visual prosthesis according to claim 34, wherein the light signals emitted by the at least one light-emitting element contain information about a position of the intraocular implant part, a quality of image data received by the intraocular implant part, a quality of a current supply of the intraocular implant part and/or about an impedance of the stimulation electrodes.

36. The visual prosthesis according to claim 32, wherein the at least one light-emitting element is configured to be arranged inside the eye so that the light signals emitted by the at least one light-emitting element can be detected by an observer via visual contact.

37. The visual prosthesis according to claim 32, wherein the at least one light-emitting element is designed as a diode that radiates light, including infrared light, which can be detected by an infrared light receiver, outside the eye.

38. The visual prosthesis according to claim 32, wherein the visual prosthesis further comprises electronic components which are required for preparing image data captured by an external camera, and also the external camera, are accommodated together with an external infrared transmitter or with an external infrared receiver in a spectacle frame.

39. A method for operating a visual prosthesis, comprising:
capturing an image using an external camera,
generating position-resolved image data from the captured image,
calculating diagnostic instructions, control instructions or stimulation instructions with a particular duration and intensity as a function of the image data,
transferring the diagnostic instructions, control instructions or stimulation instructions to a stimulation system having an intraocular implant part configured to be attached to an inside of an eye and an extraocular implant part configured to be attached to an outside of the eye, wherein the extraocular implant part further comprises an electrical control unit and wherein the electrical control unit comprises:
a current/voltage source and an impulse generator that is adapted to generate electrical stimulation impulses, wherein the impulse generator includes a retinal stimulator chip configured to receive the image data and convert the received image data into the electrical stimulation impulses, a number of stimulating electrodes in an electrode array, wherein the electrode array is included in the intraocular implant part, wherein the extraocular implant part further comprises at least one counter-electrode that is connected to the current/voltage source, arranged outside the eye, and configured to be attached to the eye;

calculating and generating electrical stimulation impulses or stimulation currents with a particular duration and intensity in the extraocular implant part and carrying out diagnostic tasks according to the diagnostic instructions, control instructions or stimulation instructions, transferring the electrical stimulation impulses or stimulation currents to the intraocular implant part, and applying the electrical stimulation impulses or stimulation currents to at least one stimulation electrode in the intraocular implant part so that at least one retinal cell or ganglion cell, which is in contact with a relevant stimulation electrode of the at least one stimulation electrode, is stimulated, amplifying the electrical stimulation impulses generated by the impulse generator with the current/voltage source, and forwarding the electrical stimulation impulses to the number of stimulation electrodes in the electrode array, wherein the number of stimulation electrodes in the electrode array and the at least one counter-electrode are arranged such that the electrical stimulation impulses forwarded to the number of stimulation electrodes flow back through the at least one counter-electrode via tissue of the eye into the current/voltage source.

40. The method according to claim 39, wherein the image data captured by the external camera are electrically evaluated or processed prior to transfer to the stimulation system in order to generate corresponding electrical stimulation impulses or stimulation currents.

41. The method according to claim 39, wherein transmission of current required for operation of the extraocular implant part and the intraocular implant part is carried out wirelessly via a bidirectional inductive interface between a radiofrequency transmitter antenna outside the eye and a radiofrequency receiver antenna of the extraocular implant part.

42. The method according to claim 39, wherein a transmission of the image data captured by the external camera or a transmission of the diagnostic instructions, control instructions or stimulation instructions is carried out wirelessly via a transmission channel or a plurality of separate transmission channels of a bidirectional inductive interface between a radiofrequency transmitter antenna outside the eye and a radiofrequency receiver antenna of the extraocular implant part.

43. The method according to claim 42, wherein data transmission between an extracorporeal part and an intracorporeal part is carried out simultaneously via separate transmission channels of the bidirectional inductive interface.

44. The method according to claim 39, wherein a transmission of the image data captured by the external camera or a transmission of the diagnostic instructions, control instructions or stimulation instructions is carried out wirelessly via an infrared interface between an infrared transmitter outside the eye and an infrared receiver inside the eye.

45. The method according to claim 39, wherein a transmission of the image data captured by the external camera or a transmission of the diagnostic instructions, control instructions or stimulation instructions is carried out as a serial data stream from an infrared receiver inside the eye via a wire connection to a digital control unit in the extraocular implant part.

46. The method according to claim 45, wherein the serial data stream from the infrared receiver inside the eye via the wire connection to the digital control unit in the extraocular implant part contains information about an address of a stimulation electrode included in the at least one stimulation electrode, from 1 to 250, and about an associated amplitude for the address of the stimulation electrode, from 0 to 1000 µA, of the stimulation impulses for the stimulation electrode, the diagnostic instructions, control instructions and/or stimulation instructions.

47. The method according to claim 45, wherein stimulation impulses or stimulation currents with a particular duration and intensity are calculated and generated by an electrical control unit of the extraocular implant part for each of the at least one stimulation electrode, with the aid of information relating to an electrode address and an amplitude of the stimulation impulses.

48. The method according to claim 47, wherein stimulation impulses or stimulation currents are transferred as a parallel signal stream from the electrical control unit of the extraocular implant part via parallel wire connections to the at least one stimulation electrode in the intraocular implant part.

49. The method according to claim 48, wherein the intraocular implant part transfers information about operating parameters via the wire connections to the extraocular implant part, in a parallel data stream.

50. The method according to claim 39, wherein a status and a functionality of an intracorporeal part of the visual prosthesis is monitored constantly via a bidirectional interface, and a corresponding malfunction is signaled in the event of a failure of the visual prosthesis or a transmission channel of the bidirectional inductive interface.

51. The method according to claim 39, wherein data transmission from an extracorporeal part to an intracorporeal part and data transmission from the intracorporeal part to the extracorporeal part are carried out alternately via a transmission channel of a bidirectional inductive interface.

52. The method according to one of claim 39, wherein data, which contain stimulation instructions with information about electrode addresses, current amplitudes, phase duration, phase ratio and/or polarity sign of the stimulation (current) impulses for the at least one stimulation electrode, are transferred from an extracorporeal part to an intracorporeal part via a bidirectional inductive interface.

53. The method according to one of claim 39, wherein data, which contain instructions for voltage measurement on one or more stimulation electrodes during the stimulation, for voltage measurement on one or more stimulation electrodes outside the stimulation, for measuring nerve action potentials with the aid of one or more stimulation electrodes and/or for measuring nerve action potentials with the aid of special measurement electrodes and an instruction to transfer the determined measurement values via a bidirectional inductive interface to an extracorporeal part of the visual prosthesis, are transferred from the extracorporeal part to an intracorporeal part via the bidirectional inductive interface.

54. The method according to claim 39, wherein data, which contain instructions for determining a status of an intracorporeal part, for recording particular status parameters, an identification number, a status report, a status of the charge balancing systems, a status of an energy supply, a temperature of the intracorporeal part or particular components and/or a moisture sensor measurement value and an instruction to transfer the ascertained measurement values via a bidirectional inductive interface to an extracorporeal part of the visual prosthesis, are transferred from the extracorporeal part to the intracorporeal part via the bidirectional inductive interface.

55. The method according to claim 39, wherein data transmission between an intracorporeal part and an extracorporeal part via a bidirectional inductive interface is carried out while using balanced coding, which has approximately the same number of zero-states and one-states.

56. The method according to claim 39, wherein data transmission between an intracorporeal part and an extracorporeal part is carried out via a bidirectional inductive interface while using Manchester coding, 4 PPM coding and/or 4 PPM+ coding.

57. The method according to claim 39, wherein data transmission between an intracorporeal part and an extracorporeal part via a bidirectional inductive interface is carried out by means of amplitude modulation of a carrier frequency, while using the 13.56 MHz ISM frequency band, the 27.12 ISM MHz frequency band, the 125 kHz ISM frequency band or the 433 MHz ISM frequency band.

58. The method according to claim 39, wherein data transmission between an intracorporeal part and an extracorporeal part via a bidirectional inductive interface is carried out by means of frequency modulation, phase modulation of a carrier frequency or a combination of these modulation methods.

59. The method according to claim 39, wherein a data carrier frequency which is separate from the frequency for an inductive energy supply, and which is modulated by means of amplitude modulation, frequency modulation, phase modulation or a combination of these modulation methods, is used for data transmission between an intracorporeal part and an extracorporeal part via a bidirectional inductive interface.

60. The method according to claim 39, wherein data transmission between an intracorporeal part and an extracorporeal part via a bidirectional inductive interface is carried out by means of load modulation of a carrier frequency by connecting and disconnecting a resistive load, a capacitive load, an inductive load or a combination of these loads.

61. The method according to claim 39, wherein diagnostic data about a status of an intracorporeal part of the visual prosthesis, measurement values for an electrode impedance of particular stimulation electrodes, measurement values for an electrical voltage which is applied to stimulation electrodes, and/or monitoring data of the status of particular stimulation electrodes, are transferred from the intracorporeal part to an extracorporeal part via a bidirectional inductive interface.

62. The method according to claim 39, wherein diagnostic data about a system status of a process control in an intracorporeal part of the visual prosthesis, information about correct transfer of data from an extracorporeal part to the intracorporeal part of the visual prosthesis, information about correct initialisation of the intracorporeal part, about correct resetting of the system status, about a status of an energy supply, about a status of particular components of the intracorporeal part, about errors in the stimulation, about correct conduct of the charge balancing between stimulation electrodes, about the duration of the charge balancing between stimulation electrodes, about the status of the electrical energy supply, about the voltage on stimulation electrodes at particular measuring times, about diagnostic data concerning a physiology of a patient, about a reading of action potentials of individual nerve cells, about reading of the sum action potentials of nerve cells, about the temperature in a region of the electronics of the intracorporeal part, about the temperature at particular points of the eye, about the internal eye pressure, about an acceleration measurement of the intracorporeal part and/or about the moisture inside a housing of the intracorporeal part, are transferred from the intracorporeal part to the extracorporeal part via a bidirectional inductive interface.

63. The method according to claim 39, wherein data transmission between an intracorporeal part and an extracorporeal part via a bidirectional inductive interface is carried out while using an error correction method, which corrects erroneously transmitted data bits by a redundancy in the coding of the data transmission.

64. The method according to claim 63, wherein Hamming coding, convolution coding, repetition coding and/or other suitable error correction methods are employed as the method for error correction.

65. The method according to claim 39, wherein data transmission between an intracorporeal part and an extracorporeal part via a bidirectional inductive interface is carried out while using an error detection method, by implementing various coding methods.

66. The method according to claim 65, wherein cyclic redundancy check (CRC) coding, parity check coding and/or repetition coding is used in order to detect errors in the data transmission between the intracorporeal part and the extracorporeal part via the bidirectional inductive interface.

67. The method according to claim 39, wherein data transmission from an extracorporeal part via a bidirectional inductive interface to an intracorporeal part is carried out with a data rate in the range of from 100 kilobits/second to 10 megabits/second or with a data rate in the range of from 1 megabit/second to 2 megabits/second.

68. The method according to claim 39, wherein data transmission from an intracorporeal part via a bidirectional inductive interface to an extracorporeal part is carried out with a data rate in the range of from 1 kilobit/second to 100 kilobits/second or with a data rate in the region of 10 kilobits/second.

69. The method according to claim 39, wherein data transmission from an extracorporeal part via a bidirectional inductive interface to an intracorporeal part and the data transmission from the intracorporeal part via the bidirectional inductive interface to the extracorporeal part are carried out with different data rates.

* * * * *